United States Patent [19]
Grun et al.

[11] Patent Number: 5,811,640
[45] Date of Patent: Sep. 22, 1998

[54] PEPPER VARIETY JZA

[75] Inventors: Paul Grun; Michael D. Orzolek, both of State College, Pa.

[73] Assignee: The Penn State Research Foundation, University Park, Pa.

[21] Appl. No.: 697,812

[22] Filed: Aug. 30, 1996

Related U.S. Application Data

[60] Provisional application No. 60/007,888 Sep. 5, 1995.

[51] Int. Cl.$^6$ ........................................................ A01H 5/00
[52] U.S. Cl. .......................... 800/200; 800/205; 800/250; 800/255; 800/DIG. 40; 47/58; 47/DIG. 1
[58] Field of Search ...................................... 800/200, 205, 800/250, 255, DIG. 40, DIG. 41; 47/58, DIG. 1; Plt./33.1

[56] References Cited

PUBLICATIONS

Cheng, S.S., The use of *Capsicum chinense* as sweet pepper cultivars and sources for gene transfer. Tomato and pepper production in the tropics. Asian Veg. Res. & Dev. Ctr. 55–62, 1989.

Greenleaf, W.H., Pepper breeding. In:Bassett, M.J. (ed) Breeding Vegetable Crops 67–134. AVI, Westport, Conn., 1986.

Jensen, R.J., McLeod, M.J., and Eshbaugh, W.H. Numerical taxonomic analyses of allozymic variation in Capsicum (Solanaceae). Taxon 28:315–327, 1979.

Pickersgill, B., Relationships betwween weedy and cultivated forms of some species of chili peppers (Genus Capsicum)., Evolution 25:683–691, 1971.

Pickersgill, B., Heiser, C.B., and McNeill, J., Numerical taxonomic studies on variation and domestication in some species of Capsicum., In: Hawkes, J.G., (eds.) The Biology and Taxonomy of Solanaceae., 679–700, 1979.

Shuh, D.M., Gene transfer of multiple flowers and pubescent leaf from *Capsicum chinense* into *Capsicum annuum* backgrounds., J. Amer. Soc. Hort. Sci., 115:499–502, 1990.

Smith, P.G., Villalon, B., and Villa, P.L. Horticultural classification of pepper grown in the United States., 22:11–13, 1987.

Subramanya, R., Transfer of genes for multiple flowers from *Capsicum chinense* to *Capsicum annuum*., HortScience 18:747–749, 1983.

Tanksley, S.D. Linkage relationships and chromosomal locations of enzyme–coding genes in pepper. (*Capsicum annuum* L.) Chromosoma 89:352–360. 1984.

Tanksley, S.D. and Iglesias–Olivas, J. Inheritance and transfer of multiple–flowered character from *Capsicum chinense* into *Capsicum annuum*., Euphytica 33:769–777, 1984.

*Primary Examiner*—Douglas W. Robinson
*Assistant Examiner*—Melissa L. Kimball
*Attorney, Agent, or Firm*—Thomas J. Monahan

[57] ABSTRACT

The novel pepper variety of the genus and species *Capsicum chinense* Jacq. described here was the product of an organized breeding program using forms of this species collected by us during several years in South America and bred via a pedigree breeding program for adaptation to growth in the northeastern U.S. It is characterized by a spreading habit, small light green elliptic leaves, small regularly 5-merous flowers with white corolla having no corolla throat markings, purple anthers, a style that exceeds the anther, two or more flowers per leaf axil, self compatibility, a low level of capsaicin so it is not a hot pepper, green pendant fruits becoming red, yellow, or orange upon maturity and having a rounded base, a usually pointed apex, and thin carpels. Fruits are about 5 cm. long and 2.5 cm wide, weigh approximately 3 grams each, and have 2–4 locules. Pedicels are long, curved, and slender. Seeds are yellow, around 3 mm. in diameter, and 1000 seeds weigh about 3 grams. The fruits contrast with those of the only other member of this species on the market in the United States, Habanero, in having the low capsaicin level so that the new variety is a mildly pungent pepper.

4 Claims, No Drawings

PEPPER VARIETY JZA

This application claims the benefit of provisional application Ser. No. 60/002,888 filed Sep. 5, 1995.

BACKGROUND OF THE INVENTION

The present invention relates to a novel and distinct pepper cultivar. The new cultivar is designated JZA and is characterized primarily by low pungency fruits.

Low-pungency forms of *Capsicum chinense* Jacq. are on the market in Latin America, but not elsewhere. *C. chinense* is distinct from *C. annuum*, forms of which constitute the major commercial peppers in the United States. The two species, are morphologically distinct, and are separated from one another by crossing and sterility barriers. *C. chinense* fills an important niche in South America as a condiment chopped into soups, rice, meat, fish, vegetable dishes and salads. The flavor enhances that of the other ingredients, and it adds interest to large segments of the diet. Only one strain of this species is on the market in the United States, the highly pungent variety Habanero, the hottest pepper presently available. The low pungency forms that are common in South America have a low level of capsaicin (8-methyl-n-vanillyl-6-nonenamide), dihydrocapsaicin (8-methyl-n-vanillyl-nonanamide), and their precursors. They are slightly warm, but not hot, so that the other inherent flavors do not disappear under the hot blast of capsaicin.

We decided to introduce low-pungency forms to the United States in 1988, made collections during several years in South America, and obtained samples from the CATIE international collection in Costa Rica and that of the U.S. Dept. of Agriculture in Griffin, Ga. Our breeding program involved two approaches: 1) pedigree breeding among the forms collected for adaptation to conditions in the northeastern U.S., particularly for earliness and yield; 2) introduction into our selected strains of genes from adapted forms of *C. annuum* and other strains of *C. chinense* by formation of hybrids followed by recurrent backcrossing combined with selection.

SUMMARY OF THE INVENTION

The variety is a strain of *C. chinense* Jacq. bred for adaptation to growth conditions in Pennsylvania. The fruits have a low level of capsaicin (72–98 Scoville units) such that they are slightly pungent sweet peppers. They contrast with the variety Habanero, the only other strain of *C. chinense* on the market in the United States, in that Habanero is extremely pungent.

DETAILED DESCRIPTION OF THE INVENTION

Plant.—This is perennial when grown in a warm climate, but is functionally annual when grown in Pennsylvania, since it is not winter hardy. Early growth produces an upright stem which branches when it is 15–30 cm. tall. Flower buds are initiated at the time of branching. Subsequent branching produces an umbrella-shaped canopy varying in height up to ca. 50 cm. with a width of ca. 40 cm. Two or more flower buds are formed in each leaf axil. The stems become woody as the plant matures.

Leaves.—The small light green elliptical leaves often show developmental abnormalities with puckering, formation of dark green and light green leaf areas, and growth contortions.

Flowers.—The regular 5-merous flowers have small sepals, a white corolla about 5 mm. in diameter. Petals lack color markings; the anthers are purple. The style, at flowering, slightly exceeds the height of the stamens. Styles and pollen do not exhibit self incompatibility.

Fruits.—The pendant fruits are up to approximately 5 cm. long, up to about 2.5 cm. wide, light or dark green when immature, and red, yellow, or orange when mature. They have a contour made of 2–5 smooth longitudinal folds running the length of the fruit. The calyx is saucer shaped, fruit base is rounded, and the apex pointed or rounded. The carpels are thin and have 2–4 locules. Fruits weigh approximately 3 grams. Pedicels are long, slender, and often curved at the fruit-end. Fruits have a low content of capsaicin, and so are not hot.

Seeds.—Seeds are yellow and 1000 weigh approximately 3 grams.

Pepper variety JZA has been deposited on Jun. 2, 1995 with American Type Culture Collection, 12301 Parklawn Dr., Rockville, Md. 20852 and given Accession Number 97188.

METHOD OF BREEDING

Collections were made during several years of samples of the species on the market in several areas in Venezuela. Samples of the species have been obtained from the CATIE collection in Turrialba, Costa Rica and the U.S. Dept. of Agriculture in Griffin, Ga. and genes from these and from northern-adapted strains of *Capsicum annuum* are being used in present breeding for later further enhancement of the strains claimed here.

Plants were germinated in the early spring and raised in greenhouses of The Pennsylvania State University at University Park, Pa., and moved, two to three months later, to the field at the Russell E. Larson Experiment Station at Rock Springs, Centre Co., Pa. Fall-germinated seeds were raised in the greenhouses of The Pennsylvania State University at University Park. Plants were bred for earliness, vigor, and yield via progeny tests in field among the Venezuelan strains.

*C. chinense* flowers are self-compatible and the uniformity of progeny plus the similarity of progeny from open pollination and manual self-pollination suggest that they are largely self-pollinated, but experimental evidence on degree of spontaneous out-crossing of this species in the field is not yet available. Most of the breeding work has involved controlled manual pollinations of bud-emasculated flowers, but in some cases seeds from spontaneous pollination were used to build up seed stocks. Seed increase of the strains that are the bases of the variety claimed here involved covering the plants in tents of tulle in the field to exclude cross-pollinating insects.

Replicated tests of selected strains of Venezuelan landraces were established at South East Experiment Station in Landisville, Pa., the Erie County Field Research Lab in North East, Pennsylvania, and at the Larson Experiment Station at Rock Springs. The best strain identified in these tests is the basis of the variety JZA.

REFERENCES

Cheng, S. S. The use of *Capsicum chinense* as sweet pepper cultivars and sources for gene transfer. Tomato and pepper production in the tropics. Asian Veg. Res. & Dev. Ctr. 55–62. 1989.

Greenleaf, W. H. Pepper breeding. In:Bassett, M. J. (ed.) Breeding Vegetable Crops 67–134. AVI, Westport, Conn. 1986.

Jensen, R. J., McLeod, M. J., and Eshbaugh, W. H. Numerical taxonomic analyses of allozymic variation in Capsicum (Solanaceae). Taxon 28: 315–327. 1979.

Pickersgill, B. Relationships between weedy and cultivated forms of some species of chili peppers (Genus Capsicum). Evolution 25: 683–691. 1971.

Pickersgill, B., Heiser, C. B., and McNeill, J. Numerical taxonomic studies on variation and domestication in some species of Capsicum. In: Hawkes, J. G., Lester, R. N., and Skelding, A. D. (eds.) The Biology and Taxonomy of Solanaceae. 679–700. Academic Press., N.Y. 1979.

Shuh, D. M. and Fontenot, J. F. Gene transfer of multiple flowers and pubescent leaf from *Capsicum chinense* into *Capsicum annuum* backgrounds. 3. Amer. Soc. Hort. Sci. 115: 499–502. 1990.

Smith, P. G., Villalon, B., and Villa, P. L. Horticulturul classificaion of pepper grown in the United States. 22: 11–13. 1987.

Subramanya, R. Transfer of genes for multiple flowers from *Capsicum chinense* to *Capsicum annuum*. HortScience 18: 747–749. 1983.

Tanksley, S. D. Linkage relationships and chromosomal locations of enzyme-coding genes in pepper (*Capsicum annuum* L.) Chromosoma 89: 352–360. 1984a.

Tanksley, S. D. and Iglesias-Olivas, J. Inheritance and transfer of multiple-flowered character from *Capsicum chinense* into *Capsicum annum*. Euphytica 33: 769–777. 1984b.

What is claimed is:

1. A new and distinct variety of pepper known as Pepper Variety JZA, ATCC Designation No. 97188, of *Capsicum chinense* Jacq. characterized by the production of low pungency fruit and adaptation for growth in the northeast United States.

2. The fruits of the variety of claim 1.

3. The seeds of the variety of claim 1.

4. Propagating material of the variety of claim 1.

* * * * *